United States Patent [19]

Cook

[11] Patent Number: 4,558,153

[45] Date of Patent: Dec. 10, 1985

[54] PREPARATION OF CARBOXYLIC ACIDS AND ESTERS

[75] Inventor: John Cook, Hull, England

[73] Assignee: BP Chemicals Limited, London, England

[21] Appl. No.: 663,773

[22] Filed: Oct. 23, 1984

[30] Foreign Application Priority Data

Oct. 28, 1983 [GB] United Kingdom ................. 8328905

[51] Int. Cl.$^4$ ..................... C07C 67/38; C07C 51/347
[52] U.S. Cl. .............................. 560/247; 260/410.9 R; 260/413; 560/1; 560/105; 560/174; 560/177; 562/400; 562/496; 562/577; 562/606
[58] Field of Search ................... 560/247, 233, 105, 1, 560/174, 177; 562/606, 496, 400, 577; 260/410.9 R, 413

[56] References Cited

U.S. PATENT DOCUMENTS

| | | | |
|---|---|---|---|
| 3,644,497 | 2/1972 | Mesich | 560/247 |
| 3,717,670 | 2/1973 | Schultz | 560/233 |
| 4,354,036 | 10/1982 | Rizakalla | 560/233 |

*Primary Examiner*—Michael L. Shippen
*Attorney, Agent, or Firm*—Brooks, Haidt, Haffner & Delahunty

[57] ABSTRACT

Carboxylic acids having two or more carbon atoms than formic acid, or esters of such carboxylic acids are prepared by reacting either formic acid or an ester of formic acid with an olefin at elevated temperature in the presence of a Group VIB metal catalyst. The Group VIB metal which is chromium, molybdenum or tungsten is suitably added as a carbonyl or carbonyl halide. In addition to the catalyst a halide promoter and a phosphorus containing copromoter may optionally be added. The process can be used, for example to prepare propionic acid or a propionic acid ester from ethylene and either formic acid of an ester of formic acid.

18 Claims, No Drawings

PREPARATION OF CARBOXYLIC ACIDS AND ESTERS

This invention relates to a process for the preparation of carboxylic acids and their esters by the reaction of a formic acid or an ester thereof with an olefin in which the formic acid or ester is added to the olefin to form a higher carboxylic acid.

The addition of a formate ester to an olefin has been previously described in U.S. Pat. No. 3,849,456 in which the reaction is catalysed by a peroxide. The reaction is relatively unselective in that it yields a broad mixture of carboxylic acid esters.

In our copending European Patent Application No. 0106656 there is described the addition of a formate ester or formic acid to an olefin using, as catalyst, a noble Group VIII metal such as iridium which has the advantage that it yields a narrower mixture of carboxylic acids or esters than the above mentioned peroxide catalysed reaction. Moreover, by appropriate adjustment of the conditions the reaction can be made highly selective in that, for example, the desired product can exceed 90% by weight of the liquid phase product.

It has now been found that certain metals of Group VIB of the Periodic Table are effective catalysts for the above mentioned reactions.

Thus, according to the present invention a process for the preparation of a carboxylic acid having at least two carbon atoms more than formic acid or ester of such an acid comprises reacting at elevated temperature formic acid or an ester of formic acid with an olefin characterised in that the reaction is carried out in the presence of an effective amount of a Group VIB metal catalyst.

Preferably a halide promoter such as an iodide is also present with the Group VIB metal.

The Group VIB metal catalyst, which may be chromium, molybdenum or tungsten is suitably added in the form of a compound which is soluble in the reactants and products under the conditions of reaction. Suitably, the Group VIB is added in the form of a carbonyl compound such as chromium hexacarbonyl, molybdenum hexacarbonyl or tungsten hexacarbonyl, a Group VIB carbonyl halide and the like.

In addition to the metal catalyst, it is preferable to add a halide promoter such as iodine or an iodide. Suitable iodides include the lower alkyl iodides such as methyl iodide, ethyl iodide and propyl iodide, and iodide salts of the Group IA and IIa metals.

The halide promoter is added in amounts such that the molar ratio of halide promoter to Group VIB metal is in the range 1:1 to 100:1 preferably from 10:1 to 20:1.

A phosphorus containing copromoter can also be added, for example, a phosphine. Preferred phosphines include trialkyl phosphines, such as tributyl phosphine, tricyclohexyl phosphine and triaryl phosphines such as triphenyl phosphine. The molar ratio of phosphorus containing copromoter to group VI metal compound is suitably from 1:1 to 10:1.

The reaction can optionally be effected in the presence of hydrogen, carbon monoxide or mixtures thereof.

The reaction can be effected in the gaseous or liquid phase. In the latter case a solvent for the liquid reactants can be employed. Suitable solvents are carboxylic acids of formula $RCO_2H$ where R is a $C_1$ to $C_8$ aliphatic, a $C_4$ to $C_8$ cycloaliphatic, a $C_7$ to $C_{12}$ aralkyl or a $C_6$ to $C_{10}$ aryl hydrocarbyl radical.

The acid or ester can itself be used as the solvent. A suitable solvent system is that provided by a mixture of methyl formate and acetic acid which under the reaction conditions establishes the equilibrium thus:

$$CHO_2CH_3 + CH_3CO_2H \rightleftharpoons CH_3CO_2CH_3 + HCO_2H$$

When employing such a solvent system it is preferred to have carbon monoxide present in the amount of from 1 to 70% by volume preferably 10 to 50% by volume of the gaseous atmosphere above the reactants.

Suitable olefins for use in the present invention are those having from 2 to 30 carbon atoms of formula:

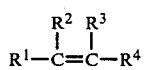

in aliphatic heteroaliphatic, acylic or cycloaliphatic form wherein $R^1$, $R^2$, $R^3$ and $R^4$ are independently either hydrogen, halogen, alkyl, alkenyl, aryl, cycloalkyl or cycloalkenyl moieties or, in a heteroaliphatic compound, are moieties containing nitrogen, phosphorus, sulphur, halogen or oxygen atoms or, in a cycloaliphatic compound $R^2$ and $R^3$ are linked. Suitable compounds having the above formula include ethylene; propylene; butene-1; butene-2; pentenes; hexenes; octenes; hexadecene; 2-methylpropene; 1,3-butadiene; 2-methyl-1,3-butadiene; 2,3-dimethyl-1,3-butadiene; styrene; methylstyrene; 3,3-dimethyl-1-butene; 1,4-hexadiene; acrolein; methyl vinyl ketone and 2-cyclohexylbutene. If desired, mixtures of these olefins may be employed.

The olefin may be mixed with the solvent and other reactants or added as a gaseous overpressure. In the latter case the pressure of gaseous olefin above the reactants is suitably at least 1 bar in excess of atmospheric pressure and is preferably in the range 10 to 100 bar.

The reaction is carried out at elevated temperature for example in the range 100° to 250° C. A preferable range of reaction temperatures is from 170° to 210° C.

In order to reduce undesirable decomposition of formic acid the concentration of formic acid is preferably maintained low, for example 25% by wt of the reaction solution and the partial pressure of olefin high, for example in the case of ethylene greater than 20 bar.

Preferably the reaction is effected in the substantial absence of oxygen.

The invention is illustrated by the following Examples.

In the Examples all the reactants and products except the ethylene were in the liquid phase, and the catalysts were employed in insolution.

EXAMPLE 1

Addition of formic acid to ethylene catalysed by $Mo(CO)_6$ in the presence of carbon monoxide and hydrogen Formic acid (50 g), methyl iodide (10 g), $Mo(CO)_6$ (1.2 g) and triphenylphosphine (3 g) were charged to a stainless steel autoclave which was pressured to 23.3 bar with ethylene. A further 26.6 bar of CO and 4.6 bar of $H_2$ were then pressed into the autoclave at room temperature. The vessel was then heated and stirred for 15 minutes at 150° C. At this temperature the initial pressure was 80 bar.

Gas chromatography (G.C.) analysis of the reaction mixture showed it to contain 10.8 g of propionic acid.

EXAMPLE 2

Addition of formic acid to ethylene catalysed by $Mo(CO)_6$ in the presence of hydrogen but no carbon monoxide A stainless steel autoclave was charged with a mixture of formic acid (50 g), methyl iodide (10 g), Mo(CO)$_6$ (1.2 g) and triphenylphosphine (3 g).

A mixture of 26.6 bar ethylene and 4 bar $H_2$ was then pressed into the autoclave at room temperature. The vessel was stirred for 30 minutes at 110° C. At this temperature the initial pressure in the reactor was 41.3 bar.

G.C. analysis of the reaction mixture showed it to contain 6.2 of propionic acid.

EXAMPLE 3

Addition of formic acid to ethylene catalysed by $W(CO)_6$ in the presence of hydrogen but no carbon monoxide Formic acid (50 g), methyl iodide (10 g), $W(CO)_6$ (2.0 g) and triphenylphosphine (3.0 g) were charged to a stainless steel autoclave which was pressured to 26.6 bar with ethylene and to a further 4 bar with $H_2$. The vessel was then stirred and heated from 110° C. to 200° C. over a period of 2.5 hours.

G.C. analysis of the reaction mixture showed it to contain 5.0 g of propionic acid.

EXAMPLE 4

Addition of methyl formate to ethylene catalysed by $Mo(CO)_6$ in the absence of hydrogen and carbon monoxide Methyl formate (50 g), methyl iodide (10 g), Mo(CO)$_6$ (1.2 g) and triphenylphosphine (3.0 g) were charged to a stainless steel autoclave which was pressured to 26.6 bar with ethylene at room temperature. The vessel was then stirred and heated at 190° C. for 2 hours.

G. C. analysis of the reaction mixture showed it to contain 2.4 g of methyl propionate.

EXAMPLE 5

Addition of methyl formate to ethylene catalysed by $W(CO)_6$ in the presence of hydrogen A stainless steel autoclave was charged with a mixture of methyl formate (50 g), methyl iodide (10 g), $W(CO)_6$ (2.0 g) and triphenylphosphine (3.0 g).

A mixture of 26.6 bar ethylene and 5.3 bar $H_2$ was then pressed into the autoclave at room temperature. The vessel was stirred for 2 hours at 200° C.

G.C. analysis of the reaction mixture showed it to contain 5.6 g of methyl propionate.

EXAMPLE 6

Reaction of ethylene in mixed methyl formate/acetic acid solvent system catalysed by $Mo(CO)_6$ A stainless steel autoclave was charged with a mixture of methyl formate (25 g), acetic acid (25 g), methyl iodide (10 g), Mo(CO)$_6$ (1.2 g) and triphenylphosphine (3.0 g).

Ethylene (26.6 bar), carbon monoxide (20 bar) and hydrogen (6.6 bar) were then pressed into the autoclave at room temperature. The vessel was stirred for 2 hours at 200° C. At this temperature the intitial pressure in the reactor was 93.3 bar.

G.C. analysis of the reaction mixture showed it to contain 15.4 g of propionic acid and 12.0 g of mthyl propionate.

EXAMPLE 7

Reaction of ethylene in mixed methyl formate/acetic acid solvent system catalysed by $W(CO)_6$ Example 6 was repeated except that the Mo(CO)$_6$ was replaced by 2.0 g of $W(CO)_6$.

G.C. analysis of the reaction mixture showed it to contain 4.3 g of propionic acid and 1.8 g of methyl propionate.

EXAMPLE 8

The procedure of Example 6 was followed except that the carbon monoxide was omitted and 5.5 bar of hydrogen was used. After 2 hours reaction at 200° C. G.C. analysis of the reaction mixture showed it to contain 1 g of propionic acid and 1.2 g of methyl propionate.

I claim:

1. A process for the preparation of a carboxylic acid, or an ester of the carboxylic acid, said carboxylic acid having at least two carbon atoms more than formic acid, which comprises reacting an olefin with formic acid or an ester of formic acid at elevated temperature in the presence of an effective amount of a Group VIB metal catalyst and a halide promoter.

2. A process as claimed in claim 1 characterised in that the Group VIB metal catalyst is a molydenum or tungsten compound.

3. A process as claimed in claim 1 characterised in that a phosphine copromoter is also employed.

4. A process as claimed in claim 1 characterised in that the olefin used is ethylene.

5. A process as claimed in claim 1 characterised in that the olefin is ethylene and the ester of formic acid is methyl formate.

6. A process as claimed in claim 1 characterised in that the reaction is carried out at a temperature in the range 170° to 210° C. and at a pressure in the range 10 to 100 bars.

7. A process as claimed in claim 1 characterised in that a solvent is employed.

8. A process as claimed in claim 7 characterised in that the solvent is a carboxylic acid of formula $RCO_2H$ where R is a $C_1$ to $C_8$ aliphatic, a $C_4$ to $C_8$ cycloaliphatic, a $C_7$ to $C_{12}$ aralkyl or a $C_6$ to $C_{10}$ aryl hydrocarbyl radical.

9. A process as claimed in claim 7 characterised in that a mixture of acetic acid and methyl formate is used as a solvent and that the reaction is carried out in the presence of carbon monoxide to coproduce the carboxylic acid and its ester.

10. A process as claimed in claim 1, wherein the olefin is ethylene, the carboxylic acid is propionic acid, and the carboxylic acid ester is a propionic acid ester.

11. A process as claimed in claim 1, wherein the olefin is ethylene, the ester of formic acid is methyl formate and the carboxylic acid ester formed is methyl propionate.

12. A process as claimed in claim 1, wherein the halide promoter is an iodide promoter.

13. A process as claimed in claim 12, wherein the iodide promoter is selected from the group consisting of a lower alkyl iodide and an iodide salt of a Group IA metal or a Group IIA metal.

14. A process as claimed in claim 1, wherein the molar ratio of halide promoter to Group VIB metal is in the range of 1:1 to 100:1.

15. A process as claimed in claim 14, wherein the molar ratio of halide promoter to Group VIB metal is in the range of 10:1 to 20:1.

16. A process as claimed in claim 3, wherein the molar ratio of phosphine containing copromoter to Group VIB metal is from 1:1 to 10:1.

17. A process as claimed in claim 3, wherein the halide promoter is methyl iodide and the phosphine compromoter is triphenylphosphine.

18. A process for the preparation of a carboxylic acid or an ester of the carboxylic acid, said carboxylic acid having at least two carbon atoms more than formic acid, which comprises reacting an olefin with formic acid or an ester of formic acid at elevated temperature in the presence of an effective amount of a Group VIB metal carbonyl compound as catalyst.

* * * * *

UNITED STATES PATENT AND TRADEMARK OFFICE
CERTIFICATE OF CORRECTION

PATENT NO. : 4,558,153
DATED : December 10, 1985
INVENTOR(S) : JOHN COOK

It is certified that error appears in the above-identified patent and that said Letters Patent is hereby corrected as shown below:

Col. 2, line 19, "acylic" should read --acyclic--

Col. 2, line 52, "in insolution" should read --in solution--

Col. 4, line 2, "mthyl" should read --methyl--

Col. 6, claim 17, lines 2-3, "com-promoter" should read --co-promoter--

Signed and Sealed this

Fourth Day of March 1986

[SEAL]

Attest:

DONALD J. QUIGG

Attesting Officer

Commissioner of Patents and Trademarks